US 6,696,694 B2

(12) United States Patent
Pastyr et al.

(10) Patent No.: US 6,696,694 B2
(45) Date of Patent: Feb. 24, 2004

(54) DISPLACEMENT DETECTING ELEMENT

(75) Inventors: Otto Pastyr, Leimen (DE); Gernot Echner, Wiesenbach (DE); Wolfgang Schlegel, Heidelberg (DE)

(73) Assignee: Deutsches Krebsforschungszentrum Stiftung des Oeffentlichen Rechts, Heidelberg (DE)

( * ) Notice: Subject to any disclaimer, the term of this patent is extended or adjusted under 35 U.S.C. 154(b) by 0 days.

(21) Appl. No.: 10/363,897

(22) PCT Filed: Aug. 14, 2001

(86) PCT No.: PCT/EP01/09364
§ 371 (c)(1),
(2), (4) Date: May 27, 2003

(87) PCT Pub. No.: WO02/23558
PCT Pub. Date: Mar. 21, 2002

(65) Prior Publication Data
US 2003/0183788 A1 Oct. 2, 2003

(30) Foreign Application Priority Data
Sep. 13, 2000 (DE) .......................... 100 45 260

(51) Int. Cl.⁷ .............................. G21K 1/04; H01L 10/38
(52) U.S. Cl. ..................... 250/505.1; 378/152; 378/153
(58) Field of Search .......................... 250/505.1, 515.1, 250/497.1, 498.1, 492.1, 492.3; 378/150, 151, 152, 153, 206, 147, 65

(56) References Cited

U.S. PATENT DOCUMENTS

| 4,672,212 A | | 6/1987 | Brahme | |
|---|---|---|---|---|
| 5,012,506 A | * | 4/1991 | Span et al. | 250/505.1 |
| 5,160,847 A | | 11/1992 | Leavitt | |
| 5,591,983 A | * | 1/1997 | Yao | 250/505.1 |
| 6,459,769 B1 | * | 10/2002 | Cosman | 250/505.1 |

FOREIGN PATENT DOCUMENTS

| DE | 38 18 735 | 12/1988 |
|---|---|---|
| DE | 38 38 662 | 5/1990 |
| DE | 195 36 804 | 4/1997 |
| DE | 196 24 780 | 1/1998 |
| EP | 0 314 214 | 5/1989 |
| GB | 2 342 552 | 4/2000 |

OTHER PUBLICATIONS

"Motorized Micro Multileaf Collimator", Leibinger Company Sales Leaflet, Jun. 1998.

* cited by examiner

Primary Examiner—John R. Lee
Assistant Examiner—James P. Hughes
(74) Attorney, Agent, or Firm—Paul Vincent

(57) ABSTRACT

The invention relates to a displacement-detecting element (1) comprising a measuring resistance (2), voltage source (3) and a displacement-dependent voltage pick off (4). The measuring resistance (2) is embodied in the form of a strip. The length of the resistor (6) corresponds to at least the maximal length of displacement (7) of the component to be detected. The invention also relates to a multileaf collimator (23) having such a displacement-detecting element (1). The aim of the invention is to produce a displacement-detecting element (a) for detecting the position of the leaves (22) in a multileaf collimator (23) in a precise and faultless manner. The displacement detecting element (1) is designed for detecting the displacement (7') of the leaves (22) in a multileaf collimator (23) in the following manner: the measuring resistance (2) or the voltage pick off point (4) are connected in a rigid manner to the leaves (22) in order to detect the displacement and another functioning element (4 or 2) is arranged in a fixed manner. At least one of these functioning elements (2, 4) is disposed in an area (33, 33', 33") of the leaves (22), which is not exposed to main radiation (34).

20 Claims, 4 Drawing Sheets

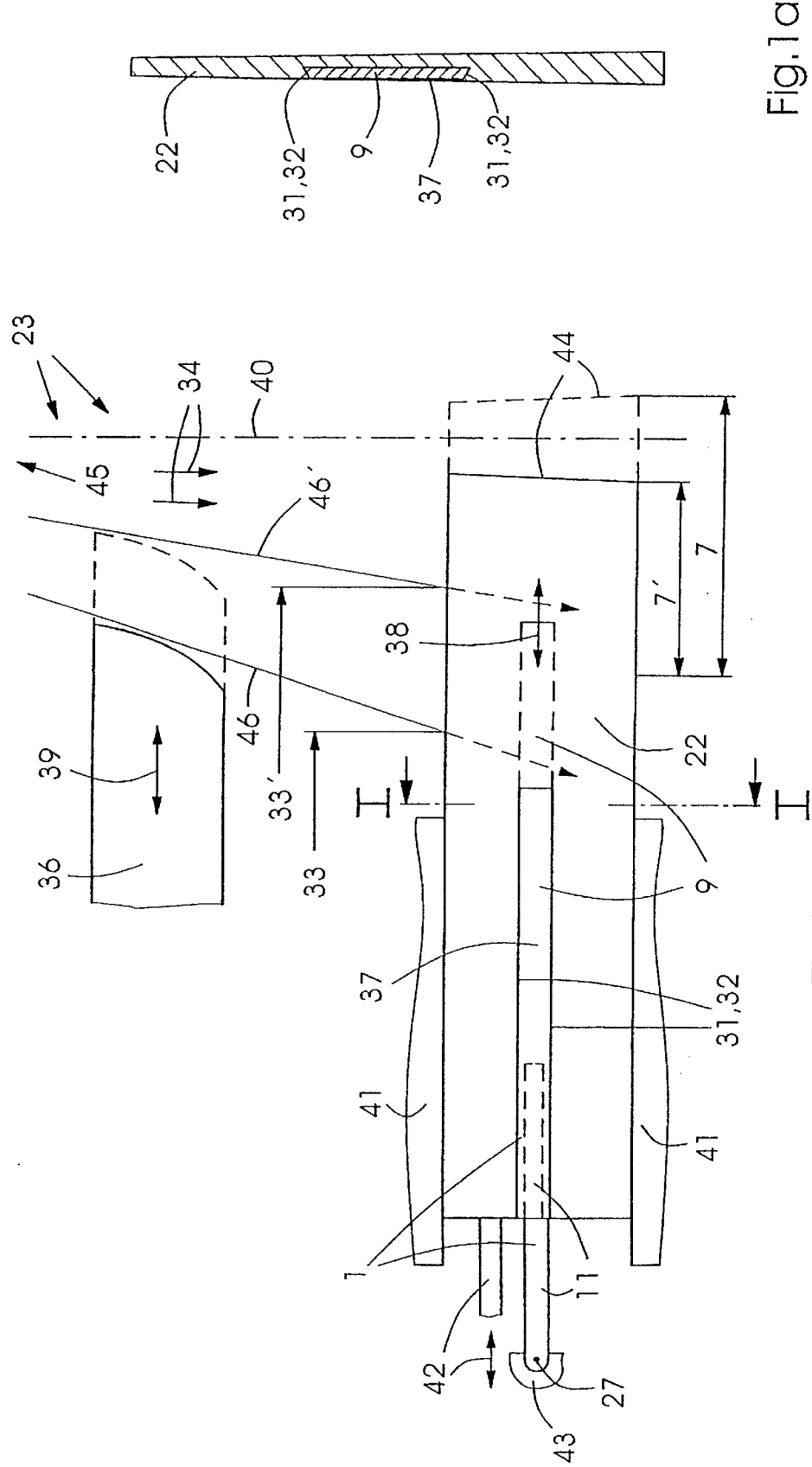

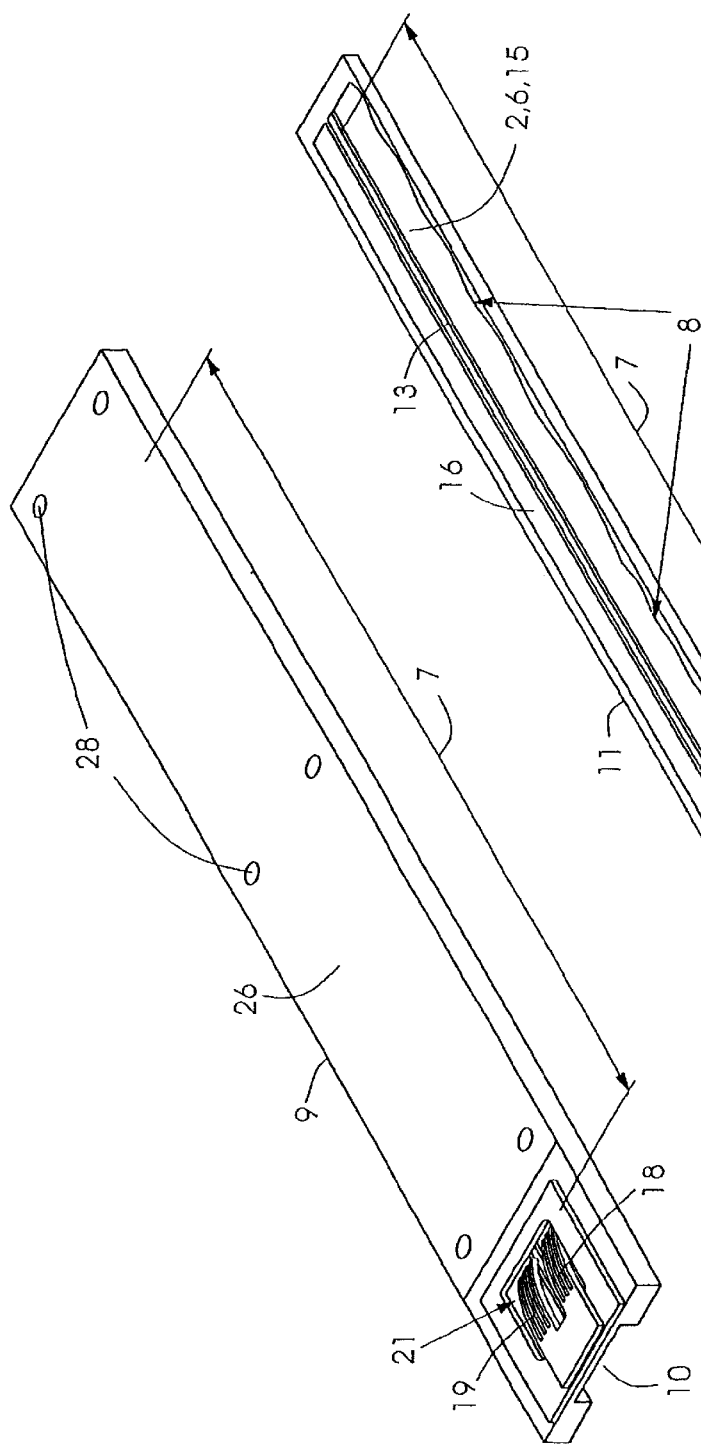

DISPLACEMENT DETECTING ELEMENT

Translation of PCT/EP01/09364 as filed on Aug. 14, 2001.

BACKGROUND OF THE INVENTION

The invention concerns a displacement detecting element comprising a measuring resistance, a voltage source, and a displacement-dependent voltage pick-off, wherein the measuring resistance is in the form of a strip and this resistance strip is at least as long as the maximum displacement length of the structural part to be detected.

The invention also concerns a multi-leaf collimator with displacement detecting elements of this type.

The principle of function of displacement detecting elements of this type is known (DE 38 38 662 A1). Those displacement detecting elements are potentiometers which are too large to be able to be directly disposed on the leaves of a multi-leaf collimator for detecting its displacement. Multi-leaf collimators are used to define a high-energy beam for tissue irradiation and have a plurality of thin, laminar leaves, which delimit and shape the beam from two sides. The leaves must be individually and exactly positioned, which requires precise detection of their positions. Conventional potentiometers do not permit detection of the position directly on the leaves due to the limited space and the disturbing influence of the radiation.

The company leaflet "Motorized Micro Multileaf Collimator 06/98" of the company Leibinger discloses arranging drives alternately above and below and opposite to the leaves in an offset and fanned-out fashion due to the limited space at the densely packed thin leaves. Each of these drives has an associated potentiometer, which serves as a displacement-detecting element. In this fashion, the displacement of the leaves is indirectly detected via determination of the position of the leaf drives.

In addition to the space requirements of the potentiometer, which increases the size of the collimators, this indirect measurement has the disadvantage that the error tolerances of the drive elements also falsify the position detection and the hysteresis produced by the play of the drive elements must be considered when the position detection adjusting direction is reversed. Since the adjusting motion must be extremely precise to protect the patient, the error tolerances of the drive elements must be kept extremely small and the hysteresis must be compensated for. In addition to its size, the stationary hysteresis-compensated arrangement of the displacement detecting elements in the above-mentioned prior art has the disadvantage that the possibilities for disposition on the leaves are limited. Moreover, if such an electrical displacement-detecting element is subjected to increased radiation of electrically charged parts, measuring errors may be produced by radiation-induced currents.

It is therefore the underlying purpose of the invention to design a displacement-detecting element of the above-mentioned type such that the position of the leaves of a multi-leaf collimator can be precisely detected, without errors.

SUMMARY OF THE INVENTION

This object is achieved in accordance with the invention in that the displacement detecting element detects the displacement of the leaves of a multi-leaf collimator by securely connecting either the measuring resistance or voltage pick-off to the leaf to be detected, with the other functional element being fixed, and at least these two functional elements are disposed in a region of the leaves which is not exposed to the main radiation.

This object is achieved with the multi-leaf collimator in that each leaf is provided with at least one displacement-detecting element of this type and all displacement detecting elements can be connected to the multi-leaf collimator control.

The invention permits position detection directly at the very thin leaves although these are densely packed next to each other without sideward gaps. In accordance with the invention, this arrangement is moreover provided in a region of the leaves, which is subjected to only relatively low radiation since the main radiation is shielded in this region. There are two possible principles of shielding which will be explained in further developments of the invention. Direct mounting of the measuring resistance or the voltage pick-off on the leaf prevents propagation of measurement errors by transmission elements and hysteresis must not be taken into consideration when the motion is reversed. A secure arrangement on the structural part to be detected is effected through direct mounting of a functional element (measuring resistance or voltage pick-off) or secure mounting of a carrier or housing. This produces an extremely high precision in a simple and inexpensive fashion.

When the multi-leaf collimators are provided with inventive displacement detecting elements, a high measuring accuracy in the region of $1/10$ to $2/10$ mm is easily obtained. This provides high precision and safety for intensity-modulated radiation therapy. The collimators can also be decreased in size since there are no potentiometers disposed on the drives.

The displacement detecting elements can be securely connected to the leaves without hysteresis via an extension on their rear side. It is particularly advantageous to directly connect them to the leaves, since the space on the rear side of the leaves thereby remains free.

Arrangement of the device components in a region of the leaves which is not exposed to the main radiation is effected by disposing the functional electrical elements of the displacement detecting element on that side of the leaves facing away from the beam to thereby shield the main radiation with full leaf thickness.

Since the leaves must have a certain length to be guided safely, they are only partially loaded with the main radiation. This permits arrangement of the electrical functional elements in the rear region of the leaves, which is not subjected to the main radiation. In contrast to the prior art arrangement, the thickness of the leaves is advantageously thereby not increased by the arrangement of the displacement detecting elements. The shielding effect of the leaves can be weakened in this region via an appropriate recess, since the leaves need not shield the main radiation at this location. This rear region of the leaves is usually shielded from the main radiation by a pre-collimator, which consists of two pairs of shielding blocks, forming a rectangle. This shielding may, of course, also be provided by a window at the radiation source.

A further development of the invention provides simple and precise adjustment of the displacement-detecting element through compensation by partial removal of material of the measuring resistance strip.

The displacement-detecting element may be directly mounted to the leaf. Since the leaves are made from radiation-absorbing metal, a non-conducting base layer must be initially disposed onto which the resistance layer is arranged. It is also possible to provide the displacement detecting element with a separate, preferably thin housing, which can be directly and rigidly mounted to the leaf. The housing may e.g. be inserted into a recess of the leaf. The housing may be designed such that it defines a recess extending along its length. A fixed tongue is displaceably disposed in this recess, wherein the displacement corresponds to at least the length of displacement of the leaf. The housing and tongue are thereby each associated with one of the functional elements, i.e. the measuring resistance or the voltage pick-off. The strip of the measuring resistance may be disposed e.g. on the tongue and the voltage pick-off on the housing. Ideally, the housing and tongue are designed as flat plastic parts. The electrical functional elements, which have at least the maximum length of displacement performed by the leaf, are located in a gap between the housing and tongue and are therefore well protected and wear and inaccuracy due to mechanical loading is prevented. In addition to the measuring resistance, the functional elements may include a conductor path for connection of the measuring resistance and a second slide contact path.

In a possible embodiment, the measuring resistance is connected to the voltage source by disposing a terminal at one end of the resistance strip and a conductor path communicates with the other end and extends parallel to the resistance strip to the other terminal of the voltage source. The resistance strip and the conductor path may moreover be disposed on the tongue wherein the resistance strip is formed as first slide contact path and a second slide contact path with a terminal is disposed parallel thereto, wherein voltage is picked-off by disposing two electrically connected wipers on the housing which slide on the slide contact paths and with means disposed between the terminals of the second slide contact path and the voltage source for converting an associated signal into displacement information.

The above-mentioned arrangement provides for a particularly advantageous further development when the wipers are disposed on the outer side of the housing and penetrate through a window in the housing to slide on the slide contact paths. This design provides a particularly flat housing potentiometer. The height can be 1.4 mm or even less. This extremely thin construction is useful in particular for the above-mentioned use in multi-leaf collimators since increasingly thinner leaves are being used to obtain more precise formation of the shape of the region to be irradiated.

Measurement may be performed e.g. in that the means for converting the signal into displacement information is a voltage meter which is calibrated to the displacement to be detected and which picks off the measured voltage at a resistance disposed between the terminal of the second slide contact path and one of the terminals of the first slide contact path or the conductor path.

If the displacement detecting element is provided with its own housing as described above, a shielding conducting layer may be disposed on its outer surface which may be set to a certain potential, e.g. the potential of the structural component, or be grounded.

In order to create very flat displacement detecting elements and/or avoid space needed for screws, the mounting is advantageously effected by providing the housing with a dovetailed outer contour, which is inserted into a complementary recess of the leaves.

The displacement-detecting element may of course be spatially designed in the most different ways in dependence on the intended use. The actual displacement detecting element circuit may also have different designs. It is essential to the invention that the functional elements are directly mounted on the leaf to be measured and are designed such that they require little space, i.e. are very flat. Direct mounting to the leaves of a multi-leaf collimator is advisable to optimize position measurement. This also permits rapid and exact change of the contours of the regions to be irradiated as defined by the multi-leaf collimators. In this fashion, a region, e.g. a tumor, can be irradiated from different directions with a rapidly and precisely adjusted shape and without time delays caused by correction of hysteresis errors when the motion is reversed.

The invention is explained below with reference to an embodiment shown in the drawing.

BRIEF DESCRIPTION OF THE DRAWING

FIG. 1 shows a first embodiment of a leaf of a multi-leaf collimator equipped in accordance with the invention;

FIG. 1a shows the leaf section I—I;

FIG. 3 shows a housing;

FIG. 4 shows a tongue of the displacement detecting element; and

FIG. 5 shows further advantageous embodiments of the displacement-detecting element.

DESCRIPTION OF THE PREFERRED EMBODIMENT

Figure 1C:
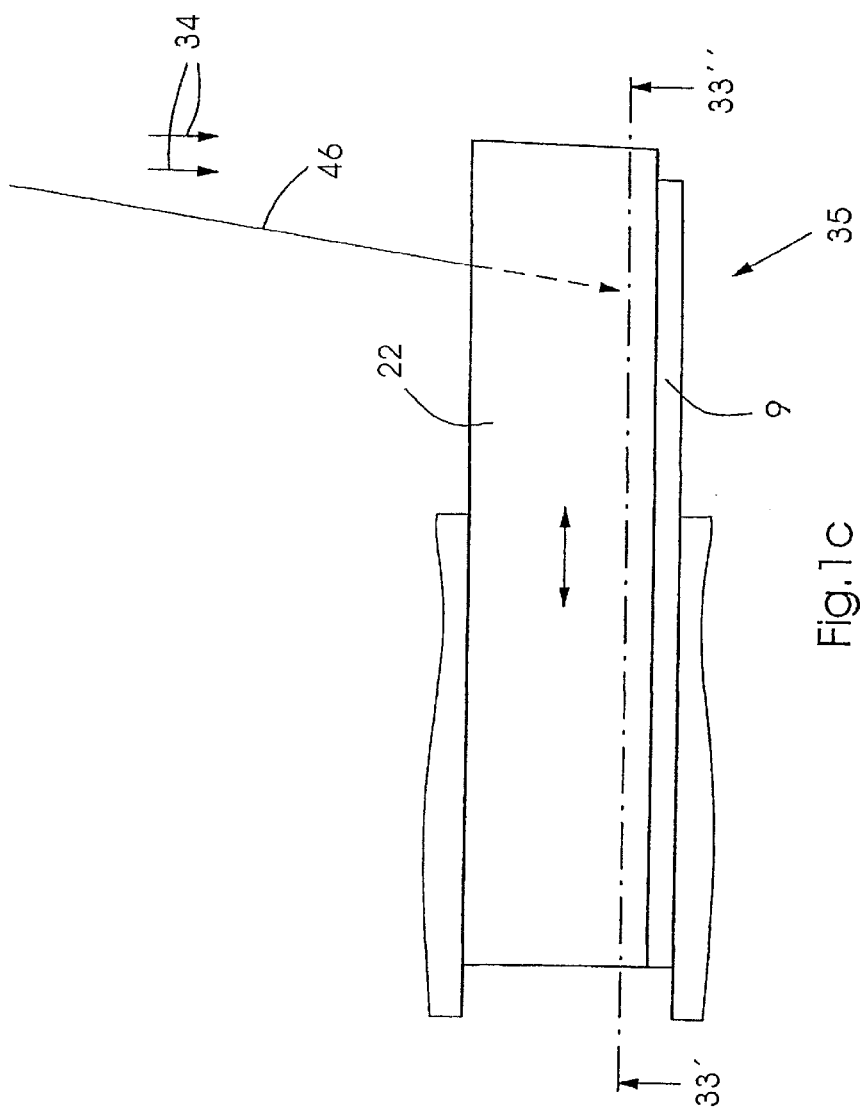
FIG. 1c shows an alternative arrangement of a displacement-detecting element on a leaf.

FIG. 1 shows a first embodiment of a leaf 22 of a multi-leaf collimator 23 configured in accordance with the invention. A displacement detecting element 1 formed as potentiometer comprising electrical functional elements, i.e. measuring resistance 2 or 15, voltage pick-off 4, conductor path 13 and slide contact path 16, is disposed in a region 33, 33' of a leaf 22 which is not subjected to the main radiation 34 of a radiation source 45 since this region 33, 33' is located in the shadow of a pre-collimator 36 which delimits the main radiation 34 corresponding to the lines 46 and 46' or another line—depending on the setting. Another setting of the leaf 22 is shown with dashed lines in which the front edge 44 was adjusted through an adjusting motion 38. To safeguard the shielding region 33', the pre-collimator 36 must also be displaced corresponding to the adjusting motion 39 (shown with dashed lines). In this embodiment, the housing 9 must be shielded in regions where no electrical functional elements are provided since the shielding material should not be weakened in areas where only the leaves 22 shield the main radiation 34. Of course, a fixed delimitation of the main radiation 36 could be provided instead of the pre-collimator 36. The displacement-detecting element 1 should then be arranged such that no electrical functional element of the displacement-detecting element 1 can move into this main radiation 46.

This embodiment also shows that the housing 9 of the displacement-detecting element 1 has a dovetailed outer contour 31, which is inserted into a complementary recess 32 of the leaf 22. The housing 9 of the displacement detecting element 1 is rigidly connected to the leaf 22 by screwing it into a recess 37 and surrounds a tongue 11 which is fixed to the collimator housing by means of a mounting 43 at its bore 27. The housing 9 may e.g. also be glued, soldered, riveted or mounted in a different fashion. In this manner, the tongue 11 can move in the housing 9 when the leaf 22 performs the adjusting motion 38 to produce, as described in detail below, a signal that is converted into displacement information through a means 5 and is processed by the control of a multileaf collimator 23. Clearly, the latter can also effect the displacement information conversion.

The illustration also shows the guidance 41 of the leaf 22 and a drive 42, which is indicated by a bar and a double arrow. The leaf 22 has an adjustment path with indicated maximum length 7.7' thereby shows the position on the adjusting path to be detected. It is thereby advantageous to be able to adjust the leaf 38 past the centerline 40 of the multi-leaf collimator 23 to produce desired shapes. The functional principle of shaping using the multi-leaf collimator 23 is also explained below. The front edge 44 of the leaf 22 is advantageously inclined parallel to the main radiation 34. The corresponding device is, however, not subject matter of this application.

FIG. 1a shows the leaf 22 in section I—I. The leaf 22 is a thin plate (shown in larger scale than in FIG. 1). One sees that the displacement-detecting element 1 must be extremely flat. It preferably has an extremely flat housing 9 to permit insertion of the housing 9 of the displacement-detecting element 1 into a recess 37 laterally disposed in the leaf 22. The housing 9 should not protrude since the next leaf borders at that location although it could also partially extend in a groove in the neighboring leaf.

Figure 1B:
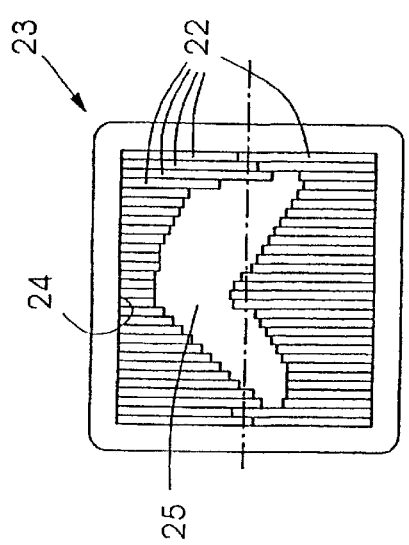
FIG. 1b schematically shows a multi-leaf collimator.

FIG. 1b schematically shows a multi-leaf collimator 23 in plan view, opposite to the direction of irradiation, wherein the delimitation 24 is shown within which the leaves 22 set the opening 25 for the radiation 34. This is effected by the drives 42 of the leaves 22 with precise positioning being obtained by the inventive displacement-detecting element 1. Since the leaves 22 are formed as densely packed lamellas of minimum width, it is important that the displacement detecting elements 1 detect the positions of the leaves 22 while having an extremely flat construction. They can be disposed e.g. in a recess 37 on the side of the leaves 22, above or below the material required for shielding. In this fashion, their positions can be directly detected and they can be protected from the main radiation 34 thereby avoiding error sources and obtaining an inexpensive solution requiring little space.

FIG. 1c shows an embodiment with an alternative arrangement of a displacement-detecting element 1 on a leaf 22. In this case, the housing 9 of the displacement detecting element 1 is disposed on the lower side of the leaf 22 so that it is completely shielded by the leaf 22 and therefore positioned in a region 33' where the main radiation 34 is largely shielded for each position of the leaf 22.

Figure 2:
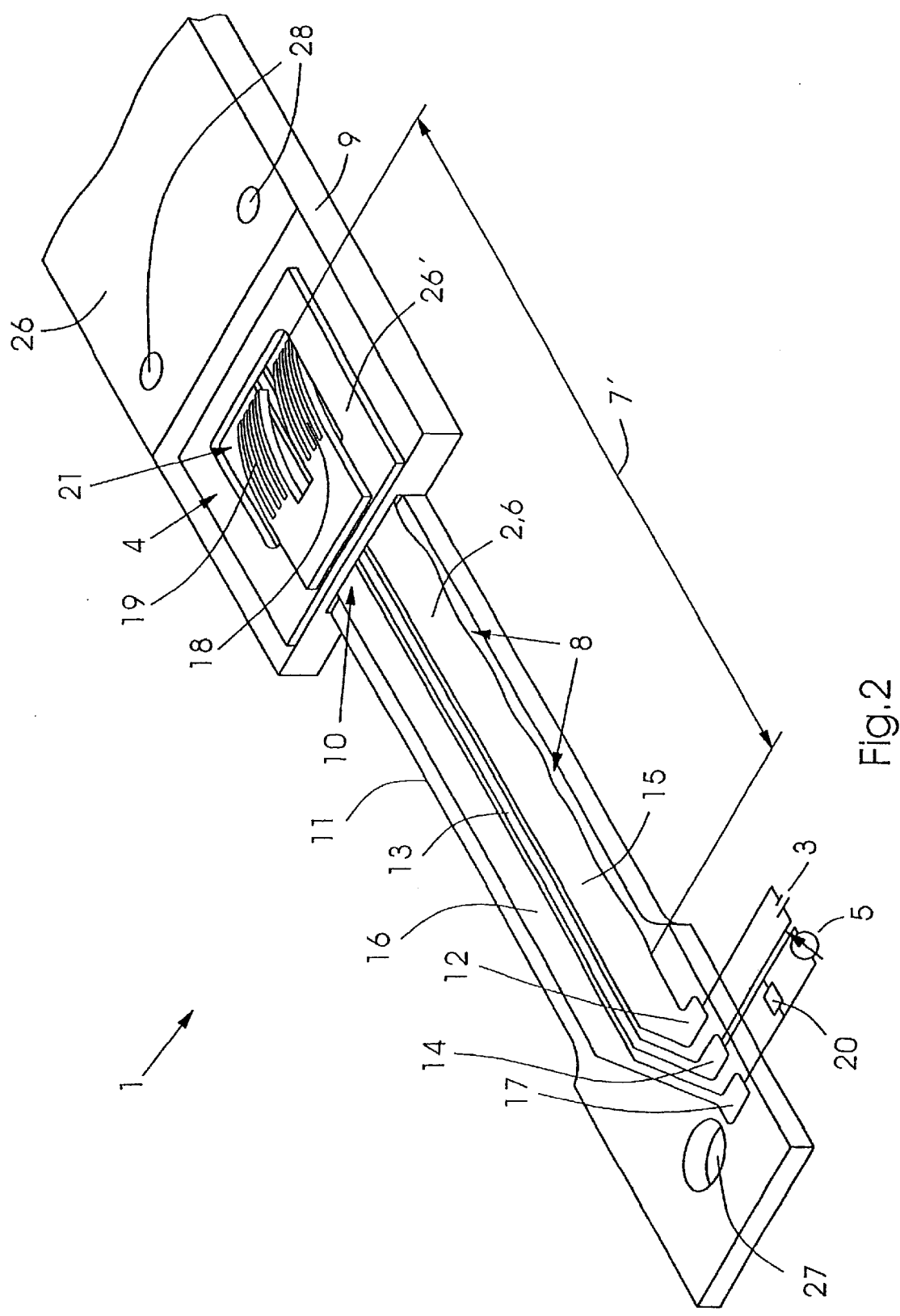
FIG. 2 shows an embodiment of the inventive displacement-detecting element.

FIG. 2 shows an embodiment of the inventive displacement-detecting element 1. This displacement-detecting element 1 comprises a housing 9 and a tongue 11, wherein the housing 9 has a recess 10 extended along the housing 9 in which the tongue 11, formed in correspondence with the recess 10, is displaceably disposed. The housing 9 can be mounted to the structural component 22 being measured via bores 28 and the bore 27 fixes the tongue 11. In this fashion, the housing 9 is displaced relative to the tongue 11 corresponding to the position changes of the leaf 22 to which the housing 9 is mounted.

To detect the position changes, the tongue 9 has a measuring resistance 2 formed as resistance strip 6. The irregular edge of the resistance strip 6 constitutes a compensation 8, which is provided by removing part of the material from the resistance strip 6 to serve for precise adjustment of the displacement-detecting element 1. The measuring resistance 2 has a terminal 12 at one end and its other end is connected to a conductor path 13 which extends parallel to the resistance strip 6 to the second terminal 14 of the measuring resistance 2, disposed next to the first terminal 12. The voltage source 3 is connected to these terminals 12 and 14. A second slide contact path 16 is disposed on the tongue 11 which extends parallel to the resistance strip 6 and the conductor path 13 and which has a terminal 17. The resistance strip 6 serves as first slide contact path 15.

The voltage pick-off 4 is effected in that the housing 9 has a first wiper 18 and a second wiper 19 which are electrically connected to thereby produce an electrical connection between the measuring resistance 2 and the second slide contact path 16 at the respective position. For this reason, all the terminals 12, 14 and 17 are located on the fixed tongue 11. This avoids cable connections subjected to motion, which could cause cable breakage. To increase the reliability of the contact, the wipers 18, 19 are fork-shaped and have several contact zones. In the position detected herein, the wipers 18, 19 are disposed on the partial length 7' of the full displacement path 7 of a leaf 22 to be detected. Advantageously, the first and second wiper 18 and 19 pass through a window 21 of the housing 9. The two wipers 18 and 19 can be resiliently disposed without requiring too much height. This embodiment permits flat construction of the displacement-detecting element 1 and mounting to very flat leaves 22.

The voltage pick-off 4 permits measurement between the terminal 17 and one of the terminals 12 or 14 by means of which the length of the respective displacement 7' and therefore the position of a leaf 22 can be determined. The measurement can be effected by disposing a resistance 20 between the terminals 17 and 12 or 14 where the voltage is picked off using a means for converting the signal into displacement information 5. This may be a voltage meter calibrated to the displacement. The resistance 20, the means 5 for converting a signal into displacement information and the voltage source 3 are symbolically drawn here. This or a corresponding function is generally integrated in the overall electronics of the device. The signals of the displacement detecting elements of all leaves are advantageously passed on to the control device of the multi-leaf collimator to thereby form the desired contours in a rapid and exact fashion.

FIG. 2 shows a conducting layer 26, which is mounted on the housing 9 for shielding. A further conducting layer 26' serves for soldering on the wipers 18 and 19. This layer 26' is very thin.

FIG. 3 shows a housing 9 of the inventive displacement-detecting element 1 which must be sufficiently long to permit a pushing motion of the tongue 11 relative to the housing 9, which corresponds, to the length of maximum displacement 7 of the leaf 22 to be detected. The other structural components correspond to those already described in FIG. 2.

FIG. 4 shows a tongue 11 of the embodiment shown in FIG. 2 wherein the measuring resistance 2 must have the above-mentioned length of displacement 7. Compensation 8 of the measuring resistance 2 was effected within this region. The figure also shows the connection between the end of the resistance strip 6 opposite to the terminal 12 and the conductor path 13, which leads to the other terminal 14. The second slide contact path 16 must also have the same length 7.

FIG. 5 shows advantageous embodiments of the displacement-detecting element 1. In one embodiment, electrical functional elements such as the measuring resistance 2, the conductor path 13 and the second slide contact path 16 are disposed in a gap 29 between the housing 9 and the tongue 11 to protect them from wear and soiling. Such a gap 29 can be realized e.g. by two steps 30 in the recess 10.

A further advantageous embodiment has the above-mentioned dovetailed outer contour 31 of the housing 9 to be able to insert the housing 9 into the leaf 22 to be detected. In this manner, a very flat displacement-detecting element 1 can be mounted to very flat leaves 22 of multi-leaf collimators 23.

This embodiment is of course only one possible realization of the invention. Depending on the design of the leaves 22, it is also possible to dispose the electrically insulated measuring resistance 2 directly on a leaf 22 and make the voltage pick-off 4 stationary. The housing 9 and tongue 11 can also have other designs. The functional elements 2 and 4 may also be disposed vice versa. Other shapes are also feasible. One leaf can have several displacement detecting elements 1 to increase the operating safety through a checking measurement and/or via increased precision of displacement detection.

LIST OF REFERENCE NUMERALS 1 displacement-detecting element (potentiometer)
2 measuring resistance (functional element)
3 voltage source
4 voltage pick-off (functional element)
5 means for converting the signal into displacement information
6 resistance strip
7 maximum length
7' part of the displacement (displacement to be detected)
8 balance
9 housing
10 recess
11 tongue
12 terminal of the measuring resistance
13 conductor path
14 connection of the measuring resistance (via conductor path)
15 first slide contact path (measuring resistance)
16 second slide contact path
17 terminal of the second slide contact path
18 first wiper (at the measuring resistance)
19 second wiper (at the second slide contact path)
20 resistance
21 window
22 leaf
23 multi-leaf collimator
24 delimitation
25 opening for radiation
26, 26' conducting layers
27 bore for mounting the tongue
28 bore for mounting the housing
29 gap
30 steps
31 dovetailed outer contour
32 complementary recess for dovetailed outer contour
33, 33', 33" region of the leaves, which is not subjected to main radiation
33 region shielded by the pre-collimator
33' region of shielding in a different position of the pre-collimator
33" region shielded by the leaves
34 main radiation
35 side of the leaves facing away from radiation
36 pre-collimator
37 recess on the leaves for insertion of the housing 9
38 double arrow: adjusting motion of the leaf
39 double arrow: adjusting motion of the pre-collimator
40 center line of the multi-leaf collimator
41 guidance of the leaf
42 drive of the leaf
43 mounting of the tongue
44 front edge of the leaves
45 radiation source
46, 46' delimitation of the main radiation

We claim:

1. A displacement detecting element for detecting displacement in a leaf of a multi-leaf collimator, the multi-leaf collimator defining a shape contour of a collimated radiation beam, the displacement detecting element comprising:
   a voltage source;
   a displacement dependent voltage pick-off; and
   a resistive strip connected between said voltage source and said voltage pick-up, said resistive strip having a length which is greater than or equal to a maximum length of displacement of the leaf, wherein one of said pick-off and said strip is connected to the leaf and the other one of said pick-off and said strip is stationary, with both said strip and said pick-off being disposed outside of the collimated radiation beam.

2. The displacement detecting element of claim 1, wherein the element is directly connected to the leaf.

3. The displacement detecting element of claim 1, wherein said pick-off and said strip are disposed on a side of the leaf facing away from a radiation source.

4. The displacement detecting element of claim 1, wherein said pick-off and said strip are disposed in a rear region of said leaf which is not exposed to the collimated beam.

5. The displacement detecting element of claim 4, wherein said rear region is shielded by a pre-collimator.

6. The displacement detecting element of claim 1, wherein a linearity of said strip is adjusted through partial removal of material from said strip.

7. The displacement detecting element of claim 1, further comprising a housing which can be mounted to the leaf.

8. The displacement wherein detecting element of claim 7, wherein said housing is inserted into a recess in the leaf.

9. The displacement detecting element of claim 8, wherein said housing defines a housing recess which extends along a length thereof, and further comprising a fixed tongue displaceably disposed in said housing recess with an amount of displaceability which is at least a maximum length of leaf displacement, wherein one of said strip and said pick-off communicates with said housing and the other one of said pick-off and said strip communicates with said tongue.

10. The displacement detecting element of claim 9, wherein said strip is located in a gap between said housing and said tongue.

11. The displacement detecting element of claim 9, wherein said strip is disposed on said tongue and said voltage pick-off is disposed on said housing.

12. The displacement detecting element of claim 11, wherein said voltage pick-off is effected via a window in said housing.

13. The displacement detecting element of claim 12, wherein said housing and said tongue are formed as flat plastic parts.

14. The displacement detecting element of claim 13, wherein said strip is connected to said voltage source by connecting one terminal of said voltage source to one end of said strip with the other end of said strip communicating with a conductor path which is disposed parallel to said strip and which is connected to the other terminal of said voltage source.

15. The displacement detecting element of claim 14, wherein said strip and said conductor path are disposed on said tongue with said strip being formed as a first slide contact path, and further comprising a second slide contact path disposed parallel to said strip, wherein said voltage pick-off comprises two electrically connected wipers disposed on said housing which slide along first and second slide contact paths, and further comprising converting means connected between said second slide contact path and said voltage source for converting a signal into displacement information.

16. The displacement detecting element of claim 15, wherein said wipers are disposed on an outer side of said housing and slide on said first and said second slide contact paths by passing through said window of said housing.

17. The displacement detecting element of claim 16, wherein said means for converting said signal into displacement information is a voltage meter calibrated to a displacement to be detected, said voltage meter evaluating a voltage across a resistor communicating with a terminal of said voltage source.

18. The displacement detecting element of claim 17, wherein said housing has a shielding conducting layer on an outer side thereof.

19. The displacement detecting element of claim 18, wherein said housing has a dove-tailed outer contour for mounting to the leaf, wherein the leaf has a complementary recess for insertion therein.

20. A multi-leaf collimator comprising displacement detecting elements according to claim 1, wherein each leaf has at least one displacement detecting element and all displacement detecting elements can be connected to a control of the multi-leaf collimator.

* * * * *